United States Patent [19]
Coston

[11] Patent Number: 5,197,876
[45] Date of Patent: Mar. 30, 1993

[54] SPLATTER GUARD FOR AIR POLISHING DENTAL DEVICE

[76] Inventor: Pamela Coston, 4132 Maple La., Powder Springs, Ga. 30073

[21] Appl. No.: 866,346

[22] Filed: Apr. 10, 1992

Related U.S. Application Data

[63] Continuation-in-part of Ser. No. 645,619, Jan. 25, 1991, abandoned.

[51] Int. Cl.$^5$ .................... A61C 1/16; A61G 17/02
[52] U.S. Cl. ................................. 433/116; 433/80
[58] Field of Search ............. 433/116, 125, 166, 80; 604/198

[56] References Cited

U.S. PATENT DOCUMENTS

| | | | |
|---|---|---|---|
| 4,424,036 | 1/1984 | Lokken | 433/116 |
| 4,611,992 | 9/1986 | Lokken | 433/116 |
| 4,850,868 | 7/1989 | Wright et al. | 433/116 |
| 4,884,968 | 12/1989 | Stien | 433/116 |
| 5,067,899 | 11/1991 | Paschal | 433/80 |

FOREIGN PATENT DOCUMENTS 2024656  11/1971  Fed. Rep. of Germany ...... 433/116

Primary Examiner—John J. Wilson
Assistant Examiner—Cindy A. Cherichetti
Attorney, Agent, or Firm—H. Jay Spiegel

[57] ABSTRACT

A splatter guard for air polishing dental devices includes a generally bell-shaped flexible member which is designed to be attached to the distal end of the air polishing device. The bell-shaped member creates a chamber which is designed to receive the back splash and splattered fluids emanating from the nozzle of the air polishing device. In this manner, the fluid from the air polishing dental device is prevented from being splattered or splashed against a patient's soft tissues, a patient's face or clothes, or the operator of the device.

4 Claims, 1 Drawing Sheet

SPLATTER GUARD FOR AIR POLISHING DENTAL DEVICE

This application is a continuation-in-part of copending application Ser. No. 07/645,619, filed Jan. 25, 1991, now abandoned.

BACKGROUND OF THE INVENTION

The present invention relates to a splatter guard for air polishing dental devices. In the prior art, devices designed to polish teeth to remove heavy plaque and the like using a combination of air and water under pressure are known. However, due to the high pressure of the air-water combination, the patients and operators face and clothes become splattered with the fluid emanating from the air polisher. Furthermore, the splashing of the spray causes saliva, blood and bacteria to be splashed out of a patient's mouth. As such, a need has developed to minimize the splattering caused by these types of dental devices.

In response to this need, Applicant has developed a splatter guard which is designed to be used with air polishing dental devices to prevent splattering of fluids and unwanted materials on a patient or operator of the device.

In the prior art, dam devices designed to protect teeth are known. Ross U.S. Pat. No. 4,600,387, Sauveur U.S. Pat. No. 4,820,155 and Gray U.S. Pat. No. 4,828,491 all disclose dental dams designed to create an operative field for dental work. None of these references teach or fairly suggest a splatter guard for use with an air polishing dental device.

Erickson U.S. Pat. No. 4,281,986 discloses a dental appliance for evacuating debris and liquid from a patient's mouth which includes a collector member and a flexible collector membrane. The collector membrane is planer in shape and is designed to facilitate the evacuation of debris and liquid from a patient's mouth. The teachings of Erickson are different from that of the present invention in that Erickson does not teach or fairly suggest a bell-shaped guard designed to prevent the spraying or splattering of fluids from a patient's mouth.

The following prior art references were made of record during the prosecution of the parent application:

Wood U.S. Pat. No. 362,808 discloses a dental polishing device having a distal facing cup in which powder is placed, with the cup being rotated to polish the teeth. The present invention differs from the teachings of Wood as contemplating a bell-shaped chamber designed to fit over the outlet conduit of an existing dental polishing machine.

Lokken U.S. Pat. No. 4,611,992 discloses a spray guard for a dental tool including a housing with a side opening designed to receive a dental polishing tool. The present invention differs from the teachings of Lokken as contemplating a bell-shaped chamber having a proximal end with an opening designed to receive the outlet conduit of an existing dental polishing device and with a distal enlarged opening.

Wright et al. U.S. Pat. No. 4,850,868 disclose a spray shield having a housing having a narrow distal end and a conically shaped proximal end. This differs from the teachings of the present invention wherein a bell-shaped member having an internal chamber is provided with the inventive member being attached over an existing outlet conduit of an existing dental polishing machine with the smaller diameter portion proximally.

German Document No. 2 024 656 to Schonauer discloses a device designed to avoid contamination of the air around a patient undergoing medical and odontological treatment as well as the appliance for their use. In the Schonauer device, a flexible and transparent sleeve is placed over the end of a dental device with a drill bit 9 or air nozzle 14 shown located adjacent the enlarged distal opening of the sleeve. The present invention differs from the teachings of Schonauer as contemplating a bell-shaped device designed to attach on the outlet conduit of an existing dental polishing device and wherein the outlet nozzle of the existing dental polishing device terminates within a proximal smaller diameter portion of the chamber thereof.

SUMMARY OF THE INVENTION

The present invention relates to a splatter guard for use with air polishing dental devices. The present invention includes the following interrelated aspects and features:

A) In a first aspect, the splatter guard for air polishing dental devices comprises a generally bell-shaped member which is attached to the distal end of the air polishing device. This member has an internal chamber with a smaller diameter proximal end widening to a larger diameter distal end having an enlarged opening.

B) The bell-shaped splatter guard is made of a flexible material so as not to injure any soft tissue in the mouth area. Furthermore, the flexible material permits the splatter guard to flex upon contact with a tooth surface such that the splatter guard prevents splattering or spraying at different angles of orientation of the air polishing device.

C) The splatter guard may be made of a silicone or plastic material and may be disposable in nature if desired.

Accordingly, it is a first object of the present invention to provide a splatter guard for air polishing dental devices.

It is a further object of the present invention to provide a bell-shaped splatter guard which prevents splashing or splattering of fluids onto a patient or operator.

It is a still further object of the present invention to provide a splatter guard made of a flexible material that minimizes injury to a patient as well as provides flexibility to maintain a shielding configuration when an air polishing machine is moved in different orientations.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
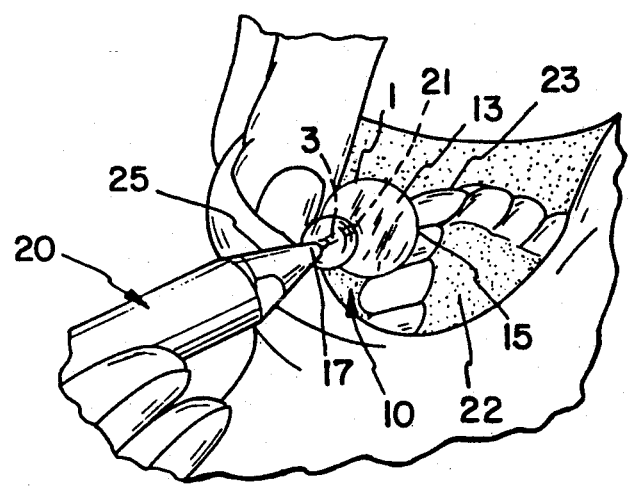
FIG. 1 shows an exemplary use of the splatter guard of the present invention.
Figure 2:
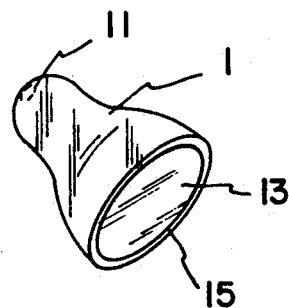
FIG. 2 shows a side perspective view of the splatter guard detached from an air polishing device.

With reference to FIGS. 1 and 2, the splatter guard of the present invention is generally designated by the reference numeral 10 and is seen to include a generally bell-shaped member 1 having an internal chamber 13 therein and a peripheral distal edge defining an enlarged opening 15. The splatter guard also includes an opening 11 which is adapted to closely receive and frictionally engage the outlet conduit 3 of an air polishing dental device 20 so as to securely attach the splatter guard to the air polishing dental device.

Figure 3:
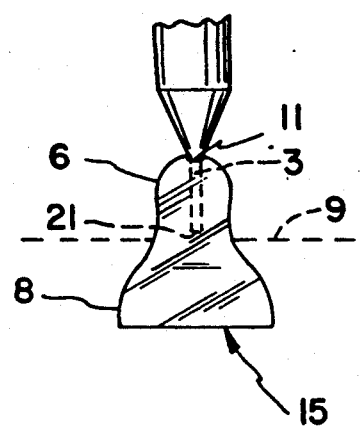
FIG. 3 shows a side view of the splatter guard attached to an air polishing dental device.

FIG. 3 shows a side view of the splatter guard as so attached and more clearly illustrates the generally bell-shaped configuration thereof.

With reference back to FIG. 1, an exemplary use of the splatter guard is illustrated in conjunction with an oral cavity. As can be seen from FIG. 1, the splatter guard 1 is attached at the distal end of a conical portion 25 of the air polishing dental device 20 at the reference numeral 17 where the conical portion 25 merges with the outlet conduit 3. The opening 11 may slightly ride up the conical surface of the portion 25 to enhance frictional retention. This attachment is achieved by inserting the conduit 3 of the air polishing device 20 through the opening 11 until the opening 11 engages the conical portion 25 of the air polishing device and is frictionally retained thereby. In use, the peripheral edge of the enlarged opening 15 of the splatter guard engages and conforms to the surface of the teeth 23 while the outlet nozzle 21 emits the fluid polishing spray. In this manner, the fluid directed from the outlet nozzle 21 at the surfaces of the teeth 23 is reflected back within the chamber 13 of the splatter guard 1 and not reflected back so as to splash out of the oral cavity 22 onto the operator or the patient. The recessing of the outlet nozzle 21 within the smaller diameter proximal end 6 of the member 1 proximal of the larger diameter distal end 8 thereof allows the operator of the device 10 to clearly view the operation thereof through the transparent walls of the member 1 as would not be the case were the outlet nozzle to lie adjacent the enlarged opening 15 of the member 1, which adjacency would cause a large degree of splashing and turbulence within the chamber 13 reducing visibility. The reference numeral 9 in FIG. 3 refers to the transition location or interface between the proximal end 6 and distal end 8 of the chamber 13. As shown in FIG. 3, the interface plane is located approximately equidistant from the attachment opening 11 and the enlarged opening 15.

The flexible nature of the generally bell-shaped splatter guard permits the peripheral edge of the enlarged opening 15 to maintain contact against a tooth surface and prevents splattering in different orientations of the nozzle 21 of the air polishing device. For example, the back surfaces or the side surfaces of the teeth would require the air polishing device to be held in a different orientation than that illustrated in FIG. 1. However, the flexible nature of the splatter guard permits portions of the splatter guard to flex so as to maintain contact or be in near proximity to tooth surfaces so as to prevent splashing or splattering of the fluid emanating from the air polishing dental device while allowing enhanced visibility of the polishing operation as compared to prior art devices.

The splatter guard may be made out of any flexible material with preferred materials including silicone. Furthermore, the splatter guard may be manufactured to be hot or cold sterilized after use or made in a disposable manner.

In use, the splatter guard in combination with an air polishing dental device prevents splashing from the fluid emanating from the device onto a patient's face, clothes or other parts of a patient's mouth. Furthermore, the splatter guard prevents splattering onto an operator's face or clothes. Finally, the splatter guard prevents the spray from the air polishing dental device from irritating the soft tissue such as the gums or lips in a patient's mouth.

As such, an invention has been disclosed in terms of a preferred embodiment thereof which fulfills each and every one of the objects of the invention as set forth hereinabove and provides a new and improved splatter guard for air polishing dental devices of great novelty and utility.

Of course, various changes, modifications and alterations in the teachings of the present invention may be contemplated by those skilled in the art without departing from the intended spirit and scope thereof. As such, it is intended that the present invention only be limited by the terms of the appended claims.

I claim:

1. A splatter guard in combination with a fluid polishing dental device, said dental device having an outlet conduit extending from a distal end thereof terminating at an outlet nozzle, said splatter guard comprising:
   a) a flexible generally bell-shaped member having an internal chamber with a smaller diameter proximal end merging with a larger diameter distal end at an interface plane, said distal end having an enlarged opening; and
   b) means for attaching said bell-shaped member adjacent said distal end of said fluid polishing dental device, said means for attaching comprising an attachment opening in said smaller diameter proximal end sized to closely receive and engage a periphery of a proximal portion of said outlet conduit with said enlarged opening facing away from said dental device and with said outlet conduit extending within said chamber, said interface plane being located approximately equidistant from said attachment opening and said enlarged opening, said outlet conduit and outlet nozzle being located proximal of said interface plane;
   c) said bell-shaped member shielding said nozzle of said fluid polishing dental device and preventing fluid emanating from said nozzle from contacting a patient or operator in undesired locations.

2. The invention of claim 1, wherein said flexible generally bell-shaped member is made of silicone.

3. The invention of claim 1, wherein said flexible generally bell-shaped member is made of plastic.

4. The invention of claim 1, wherein said attachment opening concurrently engages a distal end of a conical surface of said dental device adjacent said outlet conduit.

* * * * *